United States Patent
Viitala et al.

(10) Patent No.: US 10,016,627 B2
(45) Date of Patent: Jul. 10, 2018

(54) MEDICAL APPARATUS FOR HEATING A HEATING VOLUME DEFINED BY A SURFACE

(71) Applicant: KONINKLIJKE PHILIPS N.V., Eindhoven (NL)

(72) Inventors: Antti Johannes Viitala, Espoo (FI); Mika Petri Ylihautala, Vantaa (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 187 days.

(21) Appl. No.: 14/406,330

(22) PCT Filed: Jun. 4, 2013

(86) PCT No.: PCT/IB2013/054596
§ 371 (c)(1),
(2) Date: Dec. 8, 2014

(87) PCT Pub. No.: WO2013/186667
PCT Pub. Date: Dec. 19, 2013

(65) Prior Publication Data
US 2015/0133826 A1    May 14, 2015

Related U.S. Application Data

(60) Provisional application No. 61/658,044, filed on Jun. 11, 2012.

(51) Int. Cl.
*A61H 1/00* (2006.01)
*A61N 7/02* (2006.01)
(Continued)

(52) U.S. Cl.
CPC ...... *A61N 7/02* (2013.01); *A61B 2018/00714* (2013.01); *A61B 2090/374* (2016.02);
(Continued)

(58) Field of Classification Search
CPC .................................. A61N 7/02; A61N 7/00
See application file for complete search history.

(56) References Cited

U.S. PATENT DOCUMENTS

| 5,284,143 A | 2/1994 | Rattner |
| 6,652,473 B2 | 11/2003 | Kaufman |

(Continued)

FOREIGN PATENT DOCUMENTS

| EP | 2441492 A1 | 4/2012 |
| RU | 2366475 C2 | 9/2009 |

OTHER PUBLICATIONS

Liberman et al "Pain Palliation in Patients With Bone Metastases Using MR-Guided Focused Ultrasound Surgery: A Multicenter Study" Annals of Surgical Oncology 16 (1) p. 140-146, Nov. 11, 2008.

*Primary Examiner* — Hien Nguyen (57) ABSTRACT

The invention provides for a medical apparatus (300, 500, 600) comprising a high intensity focused ultrasound system (302), a memory containing instructions, and a processor. Execution of the instructions causes the processor to receive (100, 202) surface data (342) descriptive of the location of a surface (322). The surface data defines the location of the heating volume. Execution of the instructions further cause the processor to determine (102, 204) a set of transducer switching commands (344) using the heating location data and an ultrasound transducer element model (352) and control (104, 206) the high intensity focused ultrasound system with the set of transducer switching commands to heat the heating volume. The set of transducer switching commands comprises an intensity level for the multiple ultrasound transducer elements either above or below a predetermined intensity for controlling a cross sectional shape of the heating volume to encompass the surface.

18 Claims, 6 Drawing Sheets

(51) Int. Cl.
    *A61B 18/00*    (2006.01)
    *A61N 7/00*    (2006.01)
    *A61B 90/00*    (2016.01)

(52) U.S. Cl.
    CPC ............... *A61N 2007/0091* (2013.01); *A61N 2007/0095* (2013.01)

(56) References Cited

U.S. PATENT DOCUMENTS

| | | |
|---|---|---|
| 7,431,704 B2 | 10/2008 | Babaev |
| 7,824,348 B2 | 11/2010 | Barthe et al. |
| 7,862,510 B2 | 1/2011 | Luo |
| 2001/0031922 A1 | 10/2001 | Weng et al. |
| 2005/0107702 A1 | 5/2005 | He et al. |
| 2005/0113872 A1 | 5/2005 | Larson |
| 2006/0058707 A1 | 3/2006 | Barthe et al. |
| 2006/0094988 A1* | 5/2006 | Tosaya ............... A61H 23/0245 601/2 |
| 2007/0167781 A1 | 7/2007 | Vortman et al. |
| 2008/0275331 A1 | 11/2008 | Tseng et al. |
| 2009/0024034 A1 | 1/2009 | Moreau-Gobard et al. |
| 2009/0088623 A1 | 4/2009 | Vortman et al. |
| 2009/0326420 A1 | 12/2009 | Moonen et al. |
| 2010/0274130 A1 | 10/2010 | Anand et al. |
| 2011/0066032 A1 | 3/2011 | Vitek et al. |
| 2011/0144544 A1 | 6/2011 | Fan et al. |
| 2012/0191020 A1 | 7/2012 | Vitek |
| 2012/0253176 A1* | 10/2012 | Dumoulin ............... A61N 7/02 600/411 |
| 2013/0035582 A1 | 2/2013 | Radulescu et al. |
| 2013/0217950 A1 | 8/2013 | Partanen et al. |

\* cited by examiner

MEDICAL APPARATUS FOR HEATING A HEATING VOLUME DEFINED BY A SURFACE

CROSS-REFERENCE TO PRIOR APPLICATIONS

This application is the U.S. National Phase application under 35 U.S.C. § 371 of International Application No. PCT/IB2013/054596, filed on Jun. 4, 2013, which claims the benefit of U.S. Provisional Patent Application No. 61/658,044, filed on Jun. 11, 2012. These applications are hereby incorporated by reference herein.

TECHNICAL FIELD

The invention relates to high intensity focused ultrasound, in particular to the heating of a volume specified by a surface.

BACKGROUND OF THE INVENTION

In high intensity focused ultrasound (HIFU) an array of ultrasonic transducer elements are used to form an ultrasonic transducer. Supplying alternating current electrical power to the transducer elements causes them to generate ultrasonic waves. The ultrasonic waves from each of the transducer elements either add constructively or destructively. By controlling the phase of alternating current electrical power supplied to each of the transducer elements the focal point or volume into which the ultrasound power is focused may be controlled.

To ease the pain and suffering of some cancer patients, HIFU bone therapy has been used to destroy nerves on a restricted bone surface area. Current HIFU bone therapy applications work by placing cells or sonication points of various sizes either on the bone surface or behind it. To treat a whole bone surface, many points may need to be sonicated. Patients suffering from bone cancers may find it extremely difficult to remain still during a long procedure.

SUMMARY OF THE INVENTION

The invention provides for a medical apparatus and a computer program product in the independent claims. Embodiments are given in the dependent claims.

As will be appreciated by one skilled in the art, aspects of the present invention may be embodied as a apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as a apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

The spectroscopic magnetic resonance data may for instance be used to perform a proton spectroscopic (PS) imaging based temperature mapping method which can produce temperature maps on absolute scale. This absolute scale temperature map may therefore be used to perform a temperature calibration. This method relies on the physical principles of water proton resonance shift temperature dependence as the proton resonance frequency method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU or other temperature treatment as opposed to using a spatially homogeneous starting temperature taken as the body core temperature measured with a thermometer probe. Alternatively, the PS method can be used as a sanity check for the cumulative temperature between heat treatments outside the treatment area.

An 'ultrasound window' as used herein encompasses a window which is effectively transparent to ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a high-intensity focused ultrasound system. The high-intensity focused ultrasound system comprises an ultrasound transducer array for heating a heating volume. The ultrasound transducer array comprises multiple ultrasound transducer elements. The medical apparatus further comprises a memory for storing machine executable instructions. The medical apparatus further comprises a processor for controlling the medical apparatus.

The medical apparatus of the invention comprises an ultrasound transducer array with a plurality of transducer elements arranged in a geometrical pattern. The geometrical pattern with the location and orientation of the transducer array defines a geometric focus into which the radiation from the individual transducer elements is focused when all transducer elements are activated in-phase. The focus may be adjusted by electronically controlling the phase and optionally the amplitude, of the individual transducer elements. The phase and amplitude of the individual transducer elements are controlled by way of a set of transducer switching commands. When the phase and amplitude of the individual transducer elements are adjusted the shape of the volumetric ultrasound beam is adjusted and the size and position of the actual focus of the ultrasound radiation is changed. The individual transducer elements my even be adjusted so that no local constructive interference occurs and at best partial constructive interferences occur of a wider area, thus enlarging the focal area so that in practice no effective focusing occurs.

According to the invention, the transducer elements are controlled so that the transverse cross section of the near field of the ultrasound transducer beam emitted by the transducer array corresponds with the surface area to be treated. That is, the transverse cross section of the near field of the volumetric ultrasound beam is arranged to cover the surface area to be treated. Preferably, the transverse cross section of the near field coincides with the surface area to be treated. Notably, the transducer elements are controlled such that in the transverse cross section of the near field corresponding with the surface area to be treated the ultrasound energy density exceeds a pre-set therapeutic threshold. The ultrasound energy density in the transverse cross section causes a therapeutic effect in the surface area. For example, the ultrasound energy density in the transverse cross section causes inactivation of nerve tissue in bone surface. This alleviates pain in bone that is affected by cancer. An insight on which the invention is thus based is that in the transverse cross section of the volumetric ultrasound beam a sufficient ultrasound energy density is achieved to induce a palliative effect. Further, according to the invention, the transducer elements are controlled such that the volumetric ultrasound beam is defocused. This avoids high ultrasound energy densities in the region behind the surface area, in the propagation direction of the ultrasound radiation. The defocusing may be implemented so as to increase the size of the area e.g around the geometric focus in which to some extend constructive interference of ultrasound radiation causes an elevated ultrasound energy density. The defocusing at the geometric focus may further displace the actual focus, if that occurs, to a position where no harmful effects can occur. For example the actual focus may be displaced to a position outside of the patient to be treated. Or the actual focus region may be enlarged so that only partial constructive interference occurs without high-energy densities occurring in small areas (i.e. much smaller than the surface area), so that local hotspots are avoided. Hence, the invention enables to make use of the ultrasound energy density in the near field to induce a therapeutic, e.g. pain alleviating, effect in the surface area to be treated, while inadvertent ultrasound hotspots elsewhere are avoided.

Particularly good results are achieved when the volumetric ultrasound beam is orientated transverse, notably orthogonal, to the surface area to be treated. This orientation is achieved by way of the set of transducer switching commands which apply the phase and amplitude of the individual transducer elements which orientate the volumetric ultrasound beam's principal axis along propagation of the ultrasound radiation. The orientation of the volumetric ultrasound beam transverse to the surface area to be treated allows accurate settings of the ultrasound energy density in the near field cross section as well as accurate defocusing at the geometric focus.

Execution of the instructions causes the processor to receive surface data descriptive of the location of a surface. The surface data defines the location of the heating volume. A high-intensity focused ultrasound system focuses ultrasound onto a focal point in order to heat. These are typically described as points or sonication locations. The operation of the medical apparatus according to the invention operates slightly differently; instead of specifying sonication points a surface is described and this is used for controlling the volume that is sonicated.

Execution of the instructions further causes the processor to determine a set of transducer-switching commands using the heating location data and an ultrasound transducer element model. The ultrasound transducer element model is a model which may be used to predict the path which ultrasound generated by a particular transducer element may take. This model may be quite simple and may simply be a ray tracing type model which models the ultrasound as traveling in a direct line. There may be other more complicated models which may account for the more realistic ultrasound field generated by the transducer. The set of transducer-switching commands comprises an intensity level for each of the multiple ultrasound transducer elements either above or below a predetermined intensity for controlling a cross-sectional shape of the heating volume to encompass the surface. In other words the intensity of each of the transducer elements are either set above or below a particular level such that the ultrasound generated by the overall ultrasound transducer array matches the shape of the surface. For instance the intensity level of the predetermined intensity may be a threshold which is used to effectively turn on or off each of the individual ultrasound transducer elements.

Execution of the instructions further causes the processor to heat the heating volume by controlling the high-intensity focused ultrasound system with the set of transducer-switching commands. In some embodiments the high-intensity focused ultrasound system is not controlled with the set of transducer-switching commands only the transducer-switching commands are calculated. This embodiment may have the benefit that the medical apparatus is able to heat a relatively large region simultaneously. For instance high-intensity focused ultrasound systems typically operate by sonicating an individual point. Embodiments of the invention may be able to heat a large area simultaneously. This may be useful for applications where it is desirable to heat or treat a large region very quickly. For instance a potential application may be in the palliative treatment of bone cancers. The surface could be descriptive of the surface of a bone. The heating volume could then be used to heat the nerve cells within the heating volume and deactivate thus reducing the pain that a patient suffers during cancer.

In another embodiment the surface data could come from a medical imaging system.

In another embodiment the surface may be an ultrasound absorbing surface. An ultrasound absorbing surface as used herein is a boundary of a region which has an ultrasound attenuation that is much larger than typical soft tissue such as muscle. For instance the ultrasound absorbing region may have an absorption that is 3-20 times larger than muscle.

In another embodiment the heating volume may also be referred to as the near field of the ultrasound produced by the ultrasound transducer array.

In another embodiment each intensity level for each of the multiple transducer elements is individually assigned.

In another embodiment the predetermined intensity could be such that the transducer elements are effectively turned on or off.

In another embodiment the ultrasound transducer element model may determine which of the ultrasound transducer elements are turned on or off by projecting the heating volume onto the ultrasound transducer array. The term 'projection' as used herein is used in the geometrical sense where one surface is translated onto another surface. The ultrasound transducer element model may for instance be used to perform such a projection.

In another embodiment the ultrasound transducer element model is used to determine or is operable to determine if each of the individual transducer elements contributes ultrasound intensity above a certain level to the heating volume. This may be what essentially determines if the ultrasound transducer element is set above or below the predetermined intensity or essentially switched on or off during the operation of the high-intensity focused ultrasound system.

In another embodiment the ultrasound transducer array has a focus. The heating volume is between the ultrasound transducer and the focus. This embodiment may be beneficial because a large surface is used to specify the heating volume in a set of individual sonication points.

In another embodiment the focus is an electronically controllable focus. As used herein an electronically controllable focus is a focus of an ultrasound transducer array that may be shifted or controlled by controlling the intensity (or amplitude) and/or phase of individual ultrasound transducer elements. The transducer-switching commands further comprise a phase value for each of the multiple ultrasound transducer elements. Execution of the instructions further causes the processor to determine the phase value for each of the multiple ultrasound transducer elements to defocus the electronically controllable focus. This embodiment may be beneficial because the focus is not used as a region which is intentionally heated or sonicated. By defocusing the electronically controllable focus the chance that a region of the subject is unintentionally heated is reduced. Defocusing may be considered to be equivalent to de-phasing the focus. For instance the phase of the individual ultrasound transducer elements is selected such that at the focus destructive interference greatly reduces the intensity. In this particular embodiment the ultrasound transducer array is operated in an unfocused mode which is not the normal way for using an ultrasound transducer array from a high-intensity focused ultrasound system.

In another embodiment a transducer element chosen from the multiple transducer elements has a nearest neighbor also chosen from the multiple transducer elements. The phase value of the transducer element and the phase value of the nearest neighbor transducer element are within a predetermined phase value. This embodiment may be beneficial when the electronically controllable focus is detuned. Transducer elements which are near to each other have a phase value that was within the predetermined phase range. This may help reduce the chance of destructive interference reducing the intensity within the heating volume. This may limit the difference in phase between nearest neighbors to help keep construction and destructive interference from affecting the near field which is used for heating the heating zone.

In another embodiment execution of the instructions causes the processor to assign the multiple transducer elements with an intensity above the predetermined intensity phase values such that there is a predetermined gradient in the phase values to cause the defocusing of the electronically controllable focus. This embodiment may be beneficial because it provides a means of reducing constructive and destructive interference in the heating volume while defocusing the focus.

In another embodiment execution of the instructions further causes the processor to divide the multiple transducer elements into groups. The phase value of each of the multiple transducer elements within a particular group is identical. In other words the multiple transducer elements, particularly those that have an intensity above the predetermined intensity, are assigned or divided into groups. Each of these individual groups then has an identical phase value. The phase values of each of the groups may be selected to defocus the electronically controllable focus.

In another embodiment the ultrasound transducer element model is a ray tracing model.

In another embodiment the ultrasound transducer element model is an analytical model where the path or the intensity field produced by an ultrasound transducer element is calculated analytically.

In another embodiment the ultrasound transducer element model is a geometrical model. In this embodiment a geometrical shape is used to approximate the ultrasound field generated by an ultrasound transducer element. This may be used to predict the path of ultrasound.

In another embodiment the high-intensity focused ultrasound system further comprises a mechanical actuator for mechanically positioning the ultrasound transducer array.

In another embodiment the high-intensity focused ultrasound system further comprises a mechanical actuator for mechanically positioning the ultrasound transducer array. Execution of the instructions further cause the processor to determine actuator commands to position the actuator to concentrate ultrasonic energy in the heating volume. This may be performed using the surface data and the ultrasound transducer element model.

Execution of the instructions further causes the processor to control the actuator using the actuator commands. This embodiment may be beneficial because the ultrasound transducer array is positioned to help to shape the heating volume or near field of the ultrasound transducer array.

In another embodiment the actuator commands are operable to cause the actuator to perform any one of the following: move the actuator closer to the heating zone, move and/or rotate the actuator to increase the cross-section of the target zone, and combinations thereof.

In another embodiment execution of the instructions further causes the processor to determine an incident angle for each of the multiple ultrasound transducer elements with the surface using the ultrasound transducer element model. Execution of the instructions further causes the processor to assign the intensity level below the predetermined intensity to each of the multiple ultrasound transducer elements where the incidence angle is outside of a predetermined angular range. In this embodiment if the ultrasound generated by a particular ultrasound transducer element has an angle of incidence that is larger than a predetermined range then the ultrasound transducer element is effectively switched off. This may be beneficial in reducing the amount of scattered ultrasound which would lead to incorrect portions of a subject being heated. This for instance could be achieved using the surface data and a model to do this. This aforementioned model such as ray tracing or geometric models would lend themselves to such a calculation.

In another embodiment the high-intensity focused ultrasound system further comprises a mechanical actuator for mechanically positioning the ultrasound transducer array. Execution of the instructions further causes the processor to determine actuator commands to reduce how many of the multiple ultrasound transducer elements have an incidence angle outside of the predetermined range. Execution of the instructions further cause the processor to control the actuator using the actuator commands. Essentially in this embodiment the ultrasound transducer array is mechanically positioned in a different location to increase the number of ultrasound transducer elements which are operating. This could easily be achieved by the processor calculating several test positions using a pattern around the existing position to determine if moving the actuator to reposition the ultrasound transducer array would indeed increase the number of the multiple ultrasound transducer elements that are active.

In another embodiment the ultrasound transducer array is any one of the following: a parabolic transducer array, a flat transducer array, and a spherical transducer array.

In another embodiment the medical apparatus further comprises a medical imaging system for acquiring medical image data from an imaging volume. The heating volume is within the imaging volume. Execution of the instructions further cause the processor to acquire the medical image data and execution of the instructions further cause the processor to receive the surface data by specifying the heating location data in the medical image data. This for instance may be achieved by displaying an image or medical image rendered using the medical image data on a display and then receiving the surface data from a user interface. In other embodiments the surface data could be received by performing an image segmentation of the co-image data or an image derived from the medical image data.

In another embodiment the medical imaging system is any one of the following: a magnetic resonance imaging system, a computer tomography system, and a diagnostic ultrasound system.

In another embodiment the medical imaging system is a magnetic resonance imaging system operable for acquiring thermal magnetic resonance data from at least the heating volume. Each of the multiple ultrasound transducer elements has an adjustable amplitude or intensity level. Execution of the instructions further causes the processor to receive a treatment plan descriptive of a temperature in the heating zone. Execution of the instructions further causes the processor to acquire the thermal magnetic resonance data. Execution of the instructions further causes the processor to calculate a thermal map using the thermal magnetic resonance data. Execution of the instructions further causes the processor to determine an intensity adjustment for each of the multiple ultrasound transducer elements in accordance with the thermal map and the treatment plan. Execution of the instructions further causes the processor to control the intensity of the multiple ultrasound transducer elements using the intensity adjustment. For instance the intensity adjustment could be made to increase or decrease the temperature such that the thermal map more accurately meets the required or projected temperatures in the treatment plan.

In another aspect the invention provides for a computer program product. The computer program product comprises a computer-readable storage medium having computer executable code for execution by a processor controlling a medical apparatus. The medical apparatus comprises a high-intensity focused ultrasound system. The high-intensity focused ultrasound system comprises an ultrasound transducer array for heating the heating volume. The ultrasound transducer array comprises multiple ultrasound transducer elements. Execution of the instructions causes the processor to receive surface data descriptive of a surface. The surface defines the location of the heating volume.

Execution of the instructions further causes the processor to assign a set of transducer-switching commands using the heating location data and an ultrasound transducer element model. The set of transducer-switching commands comprises an intensity level for each of the multiple ultrasound transducer elements either above or below a predetermined intensity for controlling a cross-sectional shape of the heating volume to encompass the surface. Execution of the instructions further causes the processor to heat the heating volume by controlling the high-intensity focused ultrasound system with the set of transducer-switching commands.

In another aspect the invention provides for a method of palliative treatment using a medical apparatus. The medical apparatus comprises a high-intensity focused ultrasound system. The high-intensity focused ultrasound system comprises an ultrasound transducer array for heating a heating volume of a subject. The ultrasound transducer array comprises multiple ultrasound transducer elements. The method comprises the step of receiving surface data descriptive of the location of a bone surface within the subject. The surface data defines the location of the heating volume. The method further comprises the step of assigning a set of transducer-switching commands using the heating location data and an ultrasound transducer element model. The set of transducer-switching commands comprises an intensity level for each of the multiple ultrasound transducer elements either above or below a predetermined intensity for controlling a cross-sectional shape of the heating volume to encompass the bone surface. The method further comprises the step of heating the heating volume by controlling the high-intensity focused ultrasound system with the set of transducer-switching commands.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
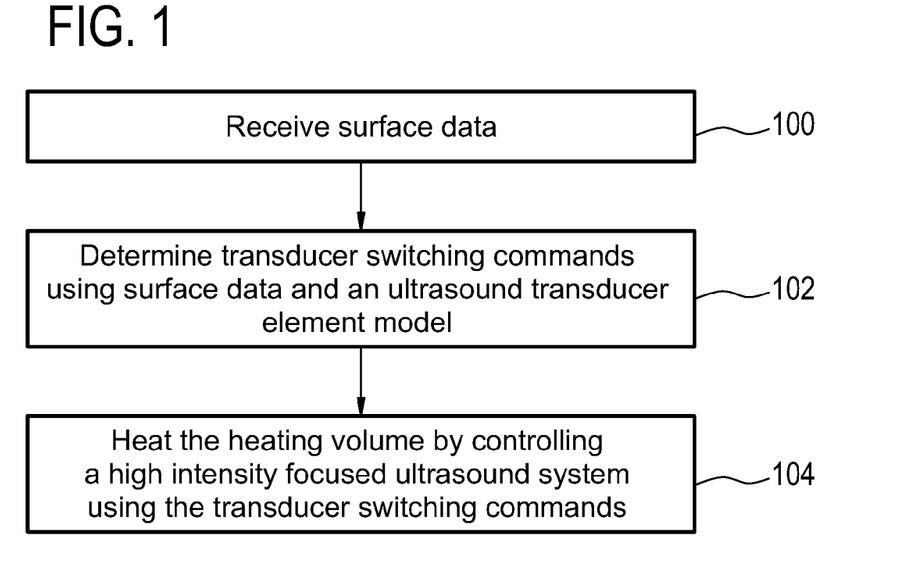
FIG. 1 shows a flow diagram which illustrate a method according to an embodiment of the invention.

FIG. 1 shows a flow diagram which illustrates a method according to an embodiment of the invention. In step 100 surface data is received. Next in step 102 transducer-switching commands for ultrasound transducer elements are determined using the surface data and an ultrasound transducer element model. Finally in step 104 the heating volume is heated by controlling a high-intensity focused ultrasound system using the transducer-switching commands.

Figure 2:
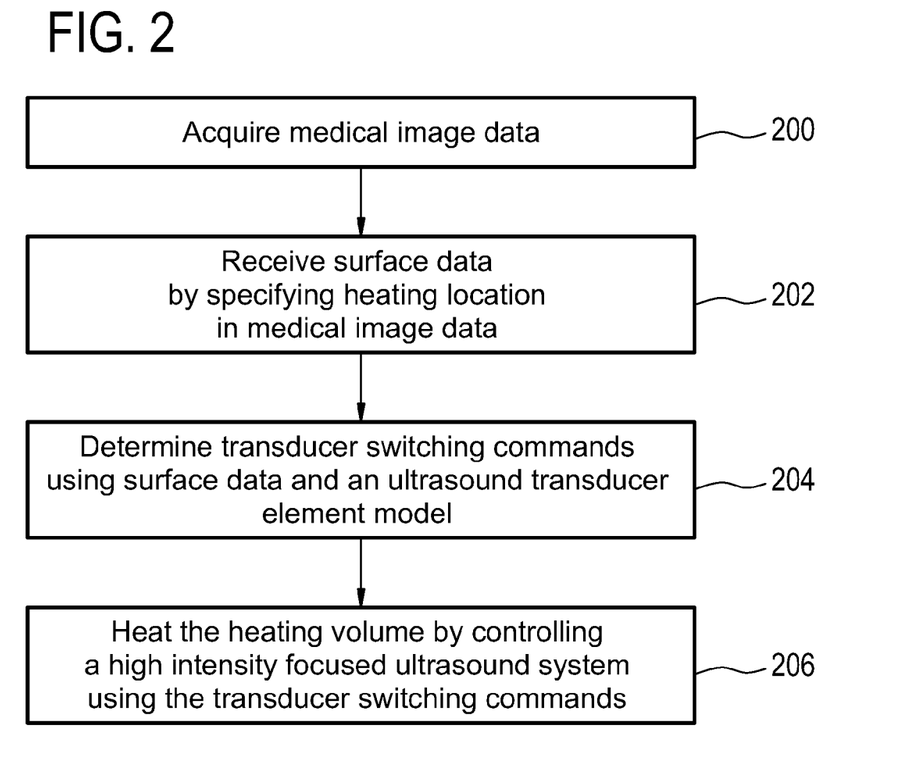
FIG. 2 shows a flow diagram which illustrate a method according to a further embodiment of the invention.

FIG. 2 shows a flow diagram which illustrates a method according to a further embodiment of the invention. First in step 200 medical image data is acquired. Next in step 202 surface data is received by specifying the heating location in the medical image data. This step may include constructing a medical image from the medical image data as well as several different methods of receiving the surface data or specifying the heating location in the medical image data. This may be received from a user interface or may be performed automatically by such things as an image segmentation module. Next in step 204 transducer-switching commands are determined using surface data and an ultrasound transducer element model. Finally in step 206 a heating volume is heated by controlling the high-intensity focused ultrasound system using the transducer-switching commands.

Figure 3:
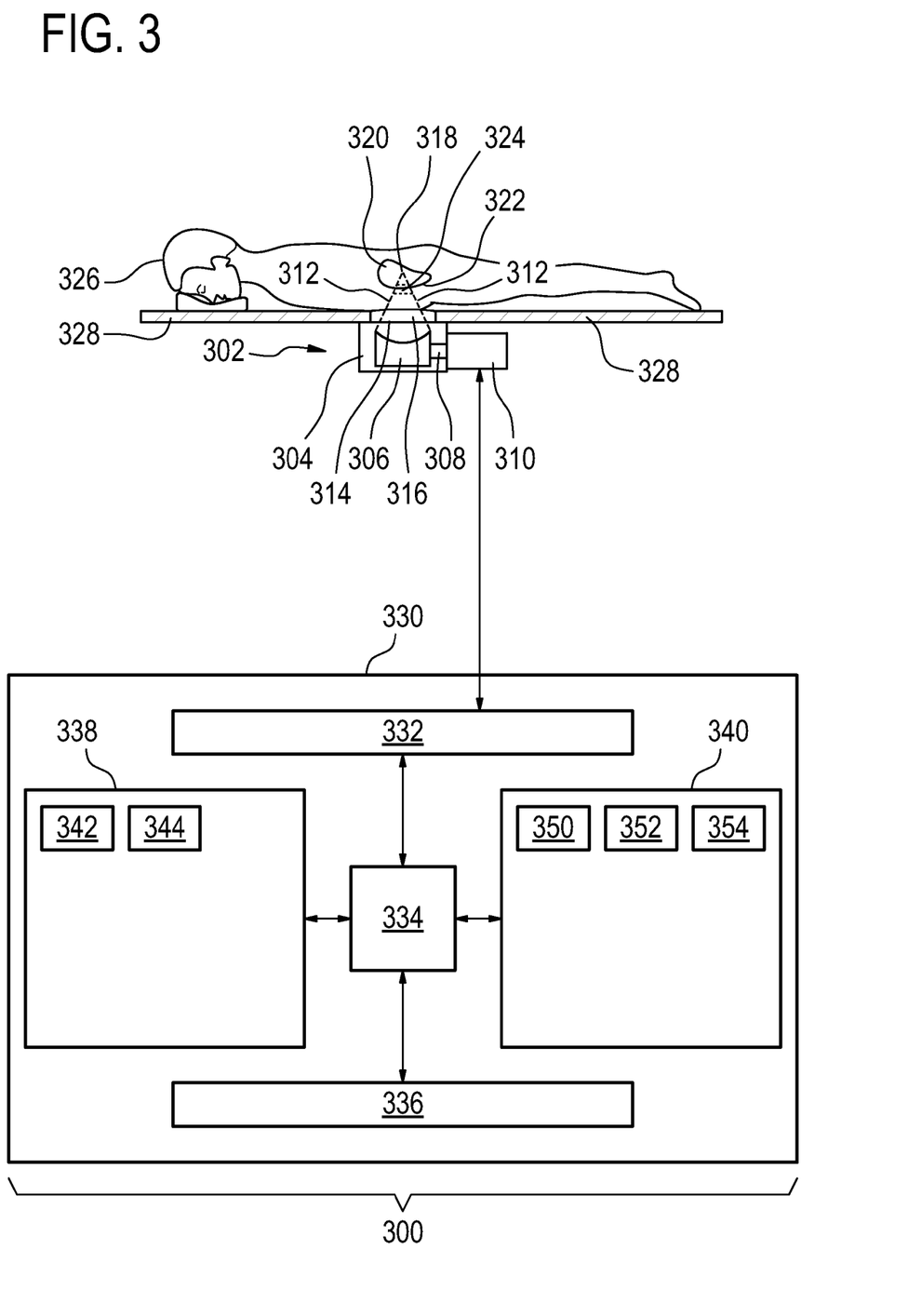
FIG. 3 illustrates a medical apparatus according to an embodiment of the invention.
Figure 4:
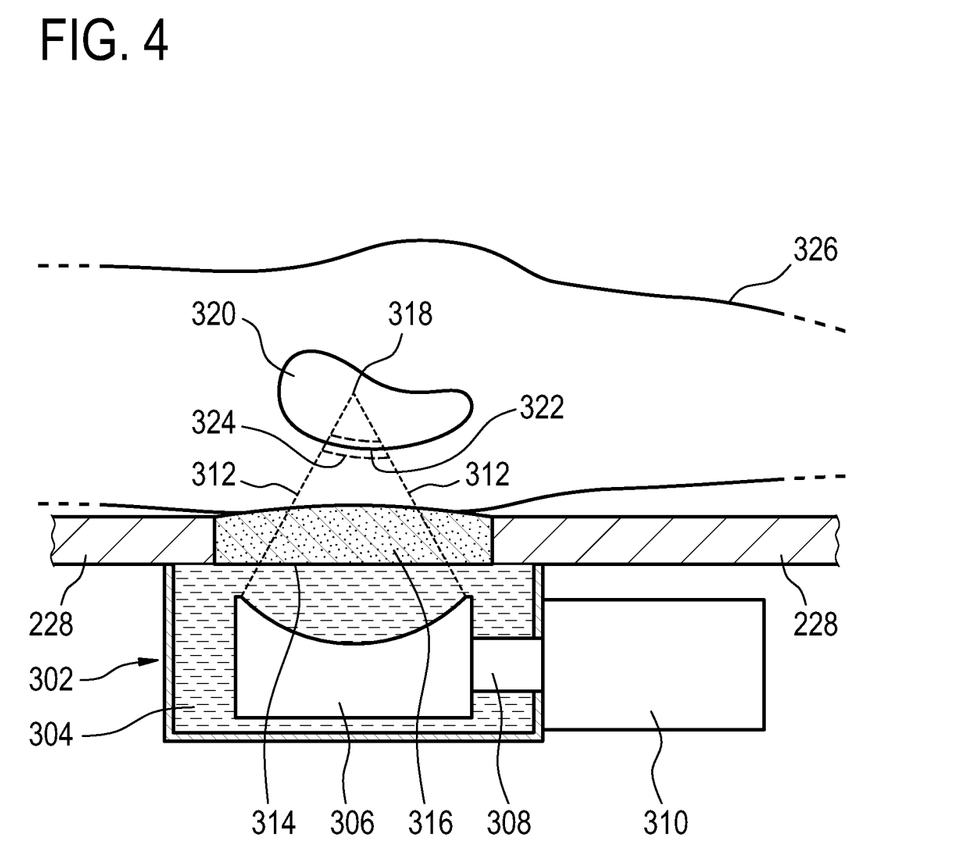
FIG. 4 shows the high intensity focused ultrasound system depicted in FIG. 3 in greater detail.

FIG. 3 illustrates a medical apparatus 300 according to an embodiment of the invention. The medical apparatus 300 comprises a high-intensity focused ultrasound system 302. FIG. 4 shows the same high-intensity focused ultrasound system 302 in greater detail. FIGS. 3 and 4 will be described together.

The high-intensity focused ultrasound system 302 comprises a fluid-filled chamber 304. Within the fluid-filled chamber 304 is an ultrasound transducer 306. Although it is not shown in this Fig. the ultrasound transducer 306 may comprise multiple ultrasound transducer elements each capable of generating an individual beam of ultrasound. This may be used to steer the location of a focal point 718 electronically by controlling the phase and/or intensity of alternating electrical current supplied to each of the ultrasound transducer elements. The focal point 318 is operable to be controlled to sonicate the target zone 304.

The ultrasound transducer 306 is connected to a mechanism 308 which allows the ultrasound transducer 306 to be repositioned mechanically. The mechanism 308 is connected to a mechanical actuator 310 which is adapted for actuating the mechanism 308. The mechanical actuator 310 also represents a power supply for supplying electrical power to the ultrasound transducer 306. In some embodiments the power supply may control the phase and/or intensity of electrical power to individual ultrasound transducer elements.

The ultrasound transducer 306 generates ultrasound which is shown as following the path 312. The ultrasound 312 goes through the fluid-filled chamber 304 and through an ultrasound window 314. In this embodiment the ultrasound then passes through a gel pad 316. The gel pad is not necessarily present in all embodiments but in this embodiment there is a recess in a subject support 328 for receiving a gel pad 316. The gel pad 316 helps couple ultrasonic power between the transducer 306 and a subject 326.

After passing through the gel pad 716 the ultrasound 712 passes through the subject 326 and is focused to a sonication point 718. The sonication point 718 is being focused within a target zone 604. The sonication point 718 may be moved through a combination of mechanically positioning the ultrasonic transducer 706 and electronically steering the position of the sonication point 718 to treat the entire target zone 604. The high-intensity focused ultrasound 312 may be brought to a focus at the focal point 318 of the high-intensity focused ultrasound transducer 306. There is a subject 326 residing on a subject support 328. The high-intensity focused ultrasound system 302 is mounted below the subject support 328.

Within the subject 326 there is an object 320. The object may for instance be bone tissue. The focal point 318 is within the object 320. The object 320 has a surface 322. There is a heating zone 324 surrounding the surface 322 that is intersected by the ultrasound 312. Instead of bringing the focus 318 and sonicating multiple points on the surface 322 it can be seen that a large region of the surface 322 may be sonicated simultaneously.

The high-intensity focused ultrasound system is connected to a hardware interface 332 of a computer system 330. The computer system further comprises a processor 334 which is connected to the hardware interface 332. The hardware interface 332 enables the processor 334 to control and operate various components of the medical apparatus 300.

The processor 334 is shown as being further connected to a user interface 336, computer storage 338, and computer memory 340.

The computer storage 338 is shown as containing surface data 342. The computer storage 338 is shown as further containing transducer-switching commands 334. The transducer-switching commands 334 may be determined using the surface data 342.

The computer memory 340 is shown as containing a control module 350. The control module 350 comprises computer-executable instructions to enable the processor 334 to control the operation and function of the medical apparatus 300. For instance the control module 350 may use the transducer-switching commands 344 to control the operation of the high-intensity focused ultrasound system 302. The computer memory 340 is shown as further comprising a transducer element model 352. The transducer element model 352 may be used by a transducer-switching command generation module 354 in conjunction with the surface data 342 to determine or calculate the transducer-switching commands 344.

Figure 5:
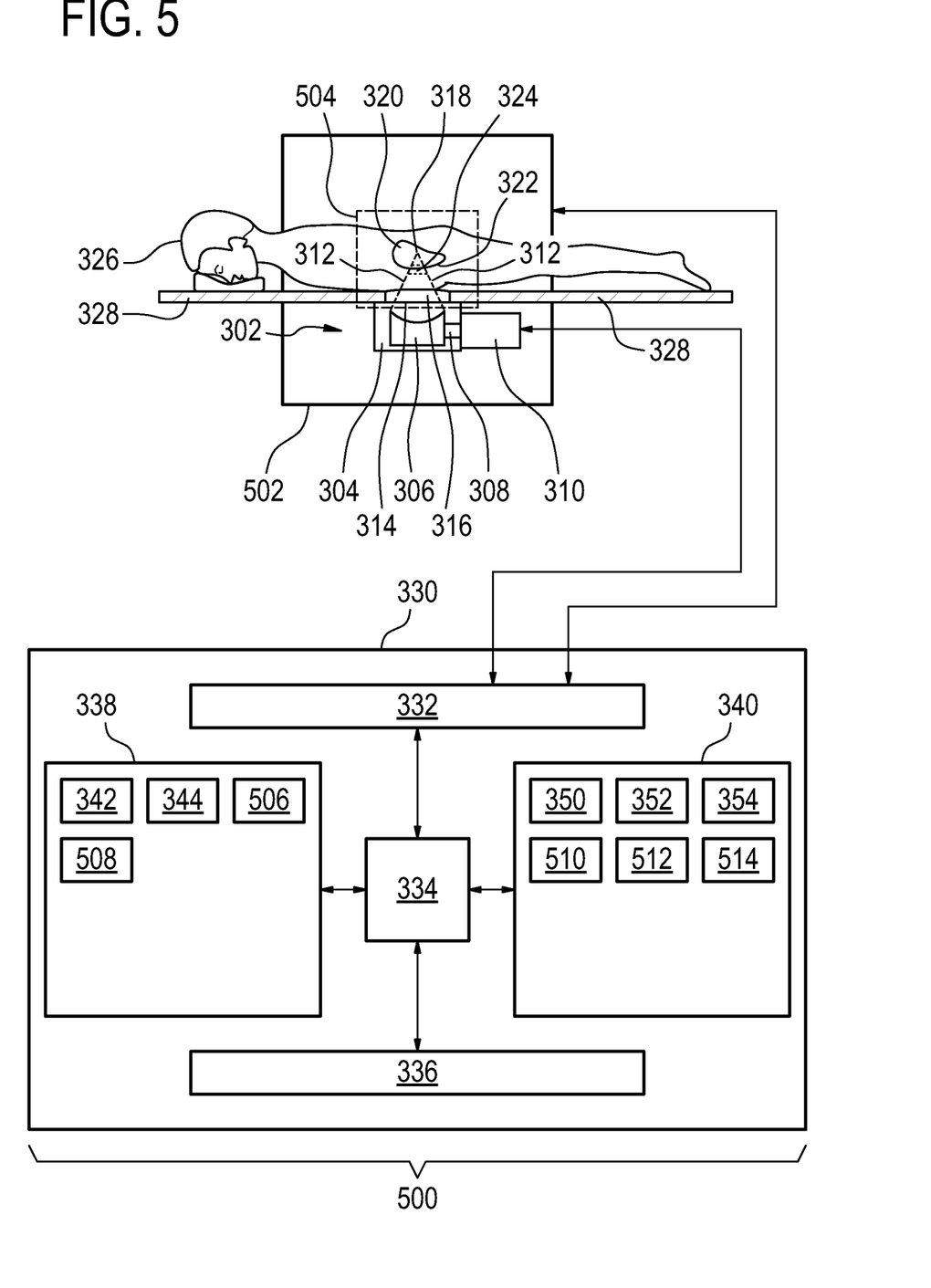
FIG. 5 illustrates a medical apparatus according to a further embodiment of the invention

FIG. 5 shows a medical apparatus 500 according to a further embodiment of the invention. The medical apparatus 500 shown in FIG. 5 is similar to that shown in FIGS. 3 and 4 except with the addition of a medical imaging system 502. In this Fig. it can be seen that the medical apparatus 500 further comprises a medical imaging system 502 operable for acquiring medical imaging data 506 from an imaging zone 504. The computer storage 338 is shown as containing the medical image data 506 and one or more medical images 508 which have been reconstructed from the medical image data 506.

The computer memory 340 is shown as containing an image reconstruction module 510. The image reconstruction module contains computer executable code which enables the processor 344 to reconstruct the medical image 508 from the medical imaging data 506. The computer memory 340 is further shown as containing an image segmentation module 512. The image segmentation module may be used in conjunction with a surface data generation module 514 to enable the processor 334 to generate the surface data 342 from the medical images 508. It should be noted that the medical imaging system 502 is intended to be a generic representation of many types of medical imaging systems such as, but not limited to: magnetic resonance imaging, computer tomography, and diagnostic ultrasound.

Figure 6:
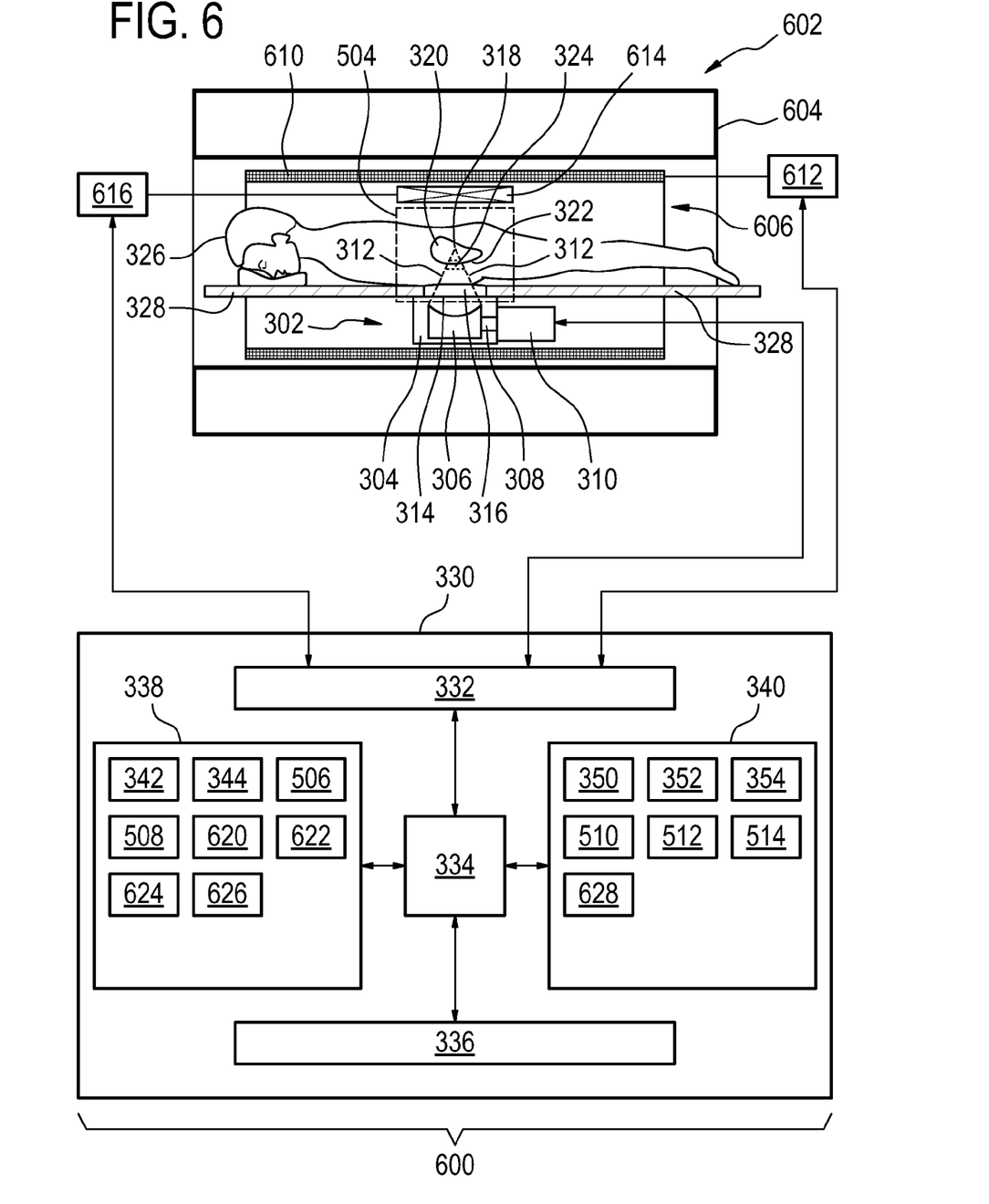
FIG. 6 illustrates a medical apparatus according to a further embodiment of the invention.

FIG. 6 shows a medical apparatus 600 according to a further embodiment of the invention. The embodiment shown in FIG. 6 is similar to that shown in FIG. 5 except in this case the medical imaging system is a magnetic resonance imaging system 602. In FIG. 6 the medical apparatus 600 further comprises a magnetic resonance imaging system 602.

The magnetic resonance imaging system 602 is shown as comprising a magnet 604. The magnet 604 is a cylindrical type superconducting magnet with a bore 606 through the center of it. The magnet 604 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone 504 where the magnetic field is strong and uniform enough to perform magnetic resonance imaging. In some embodiments the mechanical actuator/power supply 310 is located outside of the bore 606 of the magnet 604.

Also within the bore of the magnet is a magnetic field gradient coil 610 which is used for acquisition of magnetic resonance data to spatially encode magnetic spins within an imaging zone 504 of the magnet. The magnetic field gradient coil 610 is connected to a magnetic field gradient coil power supply 612. The magnetic field gradient coil is representative. Typically magnetic field gradient coils contain three separate sets of coils for spatially encoding in three orthogonal spatial directions. A magnetic field gradient power supply 612 supplies current to the magnetic field gradient coils. The current supplied to the magnetic field coils is controlled as a function of time and may be ramped and/or pulsed.

Adjacent the imaging zone 504 is a radio-frequency coil 614. The radio-frequency coil 614 is connected to a radio-frequency transceiver 616. Also within the bore of the magnet 604 is a subject 618 that is reposing on a subject support 328 and is partially within the imaging zone 504.

Adjacent to the imaging zone 504 is a radio-frequency coil 614 for manipulating the orientations of magnetic spins within the imaging zone 504 and for receiving radio transmissions from spins also within the imaging zone 504. The radio-frequency coil 614 may contain multiple coil elements. The radio-frequency coil 614 may also be referred to as a channel or an antenna. The radio-frequency coil is connected to a radio frequency transceiver 616. The radio-frequency coil 614 and radio frequency transceiver 616 may be replaced by separate transmit and receive coils and a separate transmitter and receiver. It is understood that the radio-frequency coil 614 and the radio-frequency transceiver 616 are representative. The radio-frequency coil 614 is intended to also represent a dedicated transmit antenna and a dedicated receive antenna. Likewise the transceiver 616 may also represent a separate transmitter and a separate receiver.

The magnetic field gradient coil power supply 612 and the radio-frequency transceiver 616 are also connected to the hardware interface 332 of the computer system 330. The computer system 330 and the contents of its storage 338 and memory 340 are equivalent to that as shown in FIG. 3 and FIG. 5.

The computer storage 338 is shown as further containing a pulse sequence 620. A pulse sequence as used herein is either a set of commands or data which may be used to generate commands to control the acquisition of the magnetic resonance imaging data. In this embodiment the medical imaging data 506 is magnetic resonance data. The computer storage 338 is further shown as containing a treatment plan 622. The treatment plan may contain data which is descriptive of regions of the subject 326 that should be heated above a certain temperature for a certain duration. In this embodiment the transducer-switching command generation module 354 may additionally use the treatment plan 622 in the generation of the transducer-switching commands 344. The computer storage 338 is further shown as containing thermal magnetic resonance data 624 that was acquired using a pulse sequence 620 to control the magnetic resonance imaging system 602. The computer storage 338 is shown as further containing a thermal map 626 that was reconstructed using the thermal magnetic resonance data 624.

The computer memory 340 is shown as additionally containing a high-intensity focused ultrasound control module 628. The high-intensity focused ultrasound control module 628 contains computer executable code which enables the processor 338 to function as a closed control loop to use the treatment plan 622 and the thermal map 628 to control the high-intensity focused ultrasound system 302 to sonicate or heat the heating volume 324.

Figure 7:
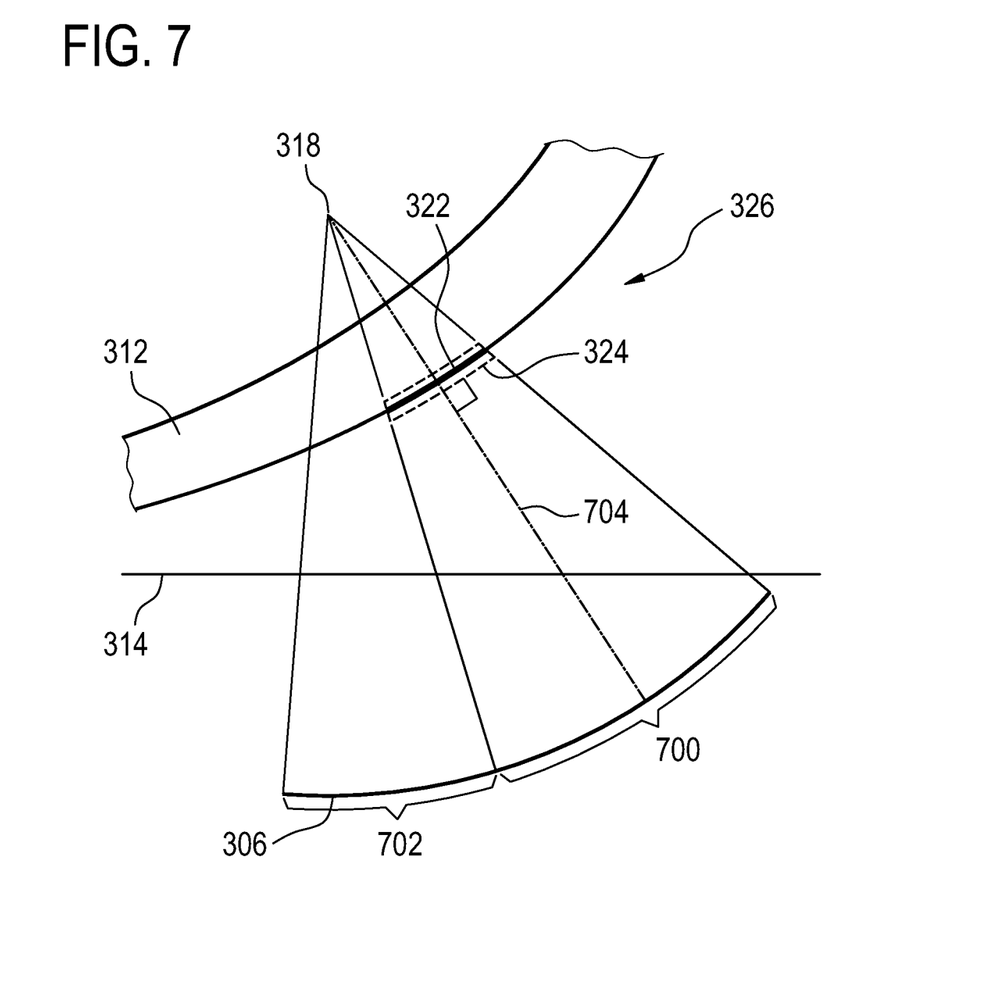
FIG. 7 shows a diagram which illustrates how the ultrasound transducer elements may be switched to heat a heating volume.

FIG. 7 shows a diagram which illustrates how the ultrasound transducer elements may be switched to heat a heating volume 324. The line 306 represents the ultrasound transducer 306 and has multiple ultrasound transducer elements across its surface. Ultrasound is focused to a focal point 318. The surface represented by 312 represents a structure such as a bone within a subject 326. The line 322 represents the surface of the object 312. The dashed lines 324 around the surface 322 represent the heating volume 324. It can be seen that on the ultrasound transducer 306 there is a region 700 where the ultrasound transducer elements are active or turned on and the second region 702 where the ultrasound transducer elements 702 are turned off. The ultrasound from the group of ultrasound transducer elements 700 intersects the surface 322 heating the heating zone 324. The ultrasound transducer 306 was positioned mechanically such that a center of mass 704 of the ultrasound beam is as perpendicular as possible with the surface 322. This increases the heating efficiency of the heating volume 324 and reduces the risk of scattered ultrasound.

While the invention has been illustrated and described in detail in the drawings and foregoing description, such illustration and description are to be considered illustrative or exemplary and not restrictive; the invention is not limited to the disclosed embodiments.

Embodiments of the invention described here may some problems related to the current bone treatment paradigm. First, in current treatment paradigm, regardless whether the focus or the near field is used for ablation, several sonications are needed for the therapy. Each sonication takes time for preparation, cooling time etc, prolonging the treatment and causing discomfort to the patient. Patients are typically quite sick and they have difficulties to stay still throughout the treatment. In the treatment paradigm described here, number of therapy sonications can be minimized, making the treatment faster and more bearable. Second, in current treatment paradigm, regardless whether the focus or the near field is used for ablation, transducer has to be always rotated mechanically to ensure that the beam angle is as perpendicular to the bone surface as possible. Sometimes the mechanism used to actuate the transducer array is unable to achieve this. Also, the design requirement for big transducer angles causes disadvantages in mechanical design. Also, repositioning of the patient to achieve bone surface angle that mechanics can support takes time and can be painful to the patient. In the treatment paradigm here, effective beam entrance angle can be changed electronically by choosing active element pattern weighted on one side of the transducer. Third, in current treatment paradigm, if near field is used for treatment, there is a danger of unintended tissue damage at the location of focus. This danger could be minimized using the defocusing technique described here. Fourth, in current treatment paradigm, it is often the case that it is difficult to position transducer so far away from the patient, that focus is localised on the desired target. This has resulted in difficulties and delays in patient positioning, and need to add several gel pads on top of the each other. Treatment paradigm described here would enable positioning of the transducer closer to the patient.

An apparatus according to an embodiment of the invention may possibly be used to perform a HIFU bone therapy. In this treatment paradigm, bone therapy a possible work flow would be as follows:

1. User identifies the bone surface area where heating is desired.
2. System/user chooses the optimal transducer mechanical position/element switch off pattern. Decision is made taking account following considerations:
   Near field will be used for the treatment
   Shape of the near field at treatment location matches the shape of the target surface as closely as possible. This way, heating is achieved everywhere in the target surface simultaneously. Since power requirements for bone treatment are relatively low, even majority of the elements can be switched off without endangering the treatment outcome.

If bigger transducer angle than what mechanics can provide is needed, element switch off pattern is chosen so that its weight is on the side of the transducer. This way the effective beam angle can be controlled without mechanically moving the transducer. (See FIG. 7)

Transducer distance from the membrane (and target) is optimized so that sharp field edge is achieved, and risk of heating in unintended regions is minimized.

3. Test sonication may be performed, if it is seen necessary.
4. Treatment sonication is performed. With careful planning, one sonication would be enough to perform the treatment.
5. To avoid unintended damage in the geometrical focus, located somewhere behind the target, phases of the individual elements are chosen so that only minimal interference occurs at the geometrical focus.

If all elements are used, simplest approach would be to change the phase of each transducer element by as many degrees as what is the element's physical coordinate on the transducer, expressed in radial coordinate system. This way opposite elements on the transducer surface would always have 180 degree phase difference. Theoretically, acoustic beams from all the elements should cancel out each others at the geometrical focus.

If some of the elements are switched off, same principle applies. First, the centre of weight of the active transducer element pattern is determined. Then the phases of the elements are chosen so, that elements at the opposite sides of this centre always cancel each other out. More symmetrical the active element pattern is, easier this becomes.

Also other methods to achieve minimal interference in the focus are sure to exist.

To further control the temperature on the bone surface, temperature imaging feedback could be used in some embodiments to control the powers of individual elements during the sonication. This way more even heating on the bone surface would be achieved. Techniques described here could also be applied for other applications beside the bone. Faster treatment with only one therapy sonication should also made use of anesthesia during the treatment easier and less risky. This may have the advantage that the planning could be done while patient is awake. Fast acting and relatively light anesthesia could be administered just for minute or two required by the treatment sonication.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 medical apparatus
302 high intensity focused ultrasound system
304 fluid filled chamber
306 ultrasound transducer
308 mechanism
310 mechanical actuator/power supply
312 path of ultrasound
314 ultrasound window
316 gel pad
318 focal point
320 object
322 surface of object
324 heating volume
326 subject
328 subject support
330 computer
332 hardware interface
334 processor
336 user interface
338 computer storage
340 computer memory
342 surface data
344 transducer switching commands
350 control module
352 transducer element model
354 transducer switching command generation module
500 medical apparatus
502 medical imaging system
504 imaging zone
506 medical imaging data
508 medical image
510 image reconstruction module
512 image segmentation module
514 surface data generation module
600 medical apparatus
602 magnetic resonance imaging system
604 magnet
606 bore of magnet
610 magnetic field gradient coil
612 magnetic field gradient coil power supply
614 radio frequency coil
616 radio frequency transceiver
620 pulse sequence
622 treatment plan
624 thermal magnetic resonance data
626 thermal map
628 high intensity focused ultrasound control module
700 active transducers
702 inactive transducers
704 center of mass of ultrasound beam

The invention claimed is:

1. A medical apparatus comprising:
a high-intensity focused ultrasound (HIFU) therapy system, provided with an ultrasound transducer array configured to emit a volumetric ultrasound beam with a geometric focus to heat treat a surface area within a subject, the ultrasound transducer array includes a plurality of ultrasound transducer elements arranged in a geometrical pattern, wherein ultrasound transducer elements of the ultrasound transducer array are activated to emit the volumetric ultrasound beam;
a memory configured for storing machine executable instructions;
a processor configured to execute the machine executable instructions to:

receive surface data, wherein the surface data is indicative of a location and shape of the surface area to be treated relative to a location of the transducer array;

calculate a set of transducer switching commands to control transducer elements so as to emit the volumetric ultrasound beam based on the surface data;

control the ultrasound transducer array to orient a principal axis of the volumetric ultrasound beam along an ultrasound propagation direction intersecting the surface area to be treated;

control the ultrasound transducer array to focus the volumetric ultrasound beam such that:

(i) the volumetric ultrasound beam has a cross section in a near field of the volumetric ultrasound beam transverse to the principal axis at the surface area to be treated, the cross section corresponding to the location and shape of the surface area to be treated;

(ii) in the cross section corresponding to the surface area to be treated, the volumetric ultrasound beam is focused to achieve constructive interference to achieve an energy density exceeding a pre-set therapeutic threshold;

(iii) the volumetric ultrasound beam is defocused in a region behind the surface area to be treated to increase a volume of the geometric focus such that the constructive interference does not occur behind the surface area to be treated therefore does not resulted in areas of high energy densities increase behind the surface area to be treated and to avoid ultrasound hotspots; and wherein the HIFU therapy system is controlled by the processor to deliver ultrasound therapy to the subject.

2. The medical apparatus as claimed in claim 1 wherein: the processor is further configured to:

determine the set of transducer switching commands using an ultrasound transducer element model wherein the set of transducer switching commands comprises an intensity level for each of the ultrasound transducer elements either above or below a predetermined intensity for controlling the cross section of the volumetric ultrasound beam to encompass the surface area to be treated; and control the high intensity focused ultrasound therapy system with the set of transducer switching commands to heat the surface area to be treated.

3. The medical apparatus of claim 2, wherein the focus of the volumetric ultrasound beam is electronically controlled, and the set of transducer switching commands further comprise a phase value for each ultrasound transducer element of the transducer array, wherein execution of the instructions causes the processor to determine the phase value for each of the plurality of ultrasound transducer elements to defocus the electronically controllable focus.

4. The medical apparatus of claim 3, wherein a selected transducer element of the transducer array has a nearest neighbor transducer element and the phase value of the selected transducer element and the phase value of the nearest neighbor transducer element are within a range of determined phase values for each of the plurality of ultrasound transducer elements.

5. The medical apparatus of claim 3, wherein execution of the instructions further causes the processor to assign the phase values of the transducer elements to cause a predetermined gradient in the phase values across the ultrasound transducer array to cause the defocusing of the electronically controllable focus.

6. The medical apparatus of claim 3, wherein execution of the instructions further causes the processor to divide the transducer elements into groups, and the phase value of each transducer element in a group is identical.

7. The medical apparatus of claim 3, wherein the high intensity focused ultrasound therapy system further comprise a mechanical actuator configured to mechanically position the ultrasound transducer array, and the processor is further configured to:

determine actuator commands to position the actuator to concentrate ultrasonic energy in the surface area to be treated using the surface data and the ultrasound transducer elements; and control the actuator using the actuator commands.

8. The medical apparatus of claim 7, wherein the actuator commands cause the mechanical actuator to perform anyone of the following: move the actuator closer to the surface area to be treated, move and/or rotate the actuator to increase the cross section and shape of the volumetric ultrasound beam at the surface area to be treated, and combinations thereof.

9. The medical apparatus of claim 8, wherein the processor is further configured to:

determine an incidence angle relative to the surface area to be treated for each of the ultrasound transducer elements using the ultrasound transducer element model; and assign the intensity level below the predetermined intensity to each of the plurality of ultrasound transducer elements where the incidence angle is outside of a predetermined angular range.

10. The medical apparatus of claim 9, wherein the processor is further configured to:

determine actuator commands to reduce how many of the ultrasound transducer elements have an incidence angle outside of the predetermined range; and control the actuator using the actuator commands.

11. The medical apparatus of claim 10, wherein the medical apparatus further includes a medical imaging system configured to acquire medical image data from an imaging volume, the imaging volume including a heating volume, and the processor is further configured to:

acquire the medical image data and receive the surface data by specifying a heating location in the medical image data.

12. The medical apparatus of claim 11, wherein the medical imaging system is a magnetic resonance imaging system operable for acquiring thermal magnetic resonance data from at least a target volume, wherein each of the ultrasound transducer elements have an adjustable intensity, and the processor is further configured to:

receive a treatment plan contained in computer storage, the treatment plan descriptive of a target temperature of the surface area to be treated;

acquire the thermal magnetic resonance data;

calculate a thermal map using the thermal magnetic resonance data;

determine an intensity adjustment for each of the plurality of ultrasound transducer elements in accordance with the thermal map and the treatment plan; and control the intensity of the plurality of ultrasound transducer element using the intensity adjustment.

13. A non-transitory computer readable medium carrying a computer program having computer executable code for execution by a processor controlling a medical apparatus, wherein the medical apparatus comprises a high intensity focused ultrasound system, wherein the high intensity focused ultrasound system comprises an ultrasound transducer array for heating a heating target volume, wherein the ultrasound transducer array comprises multiple ultrasound transducer elements, wherein execution of the instructions causes the processor to:

receive surface data descriptive of a location and shape of a surface area of a heated target volume to be treated, wherein the surface data defines the location and shape of the heating target volume;

assign a set of transducer switching commands using the received surface data and an ultrasound transducer element model, wherein the set of transducer switching commands comprises an intensity level for each of the multiple ultrasound transducer elements either above or below a predetermined intensity for controlling a cross sectional shape of the heating target volume to encompass the surface area;

control the ultrasound transducer array such that:
(i) the ultrasound transducer array emits a volumetric ultrasound beam having a cross section in a near field at the surface area transverse to a principal axis of the volumetric ultrasound beam, the cross section of the volumetric ultrasound beam corresponding to the surface area of the heating target volume defined by the surface area;
(ii) in the cross section corresponding to the surface area, the volumetric ultrasound beam has an energy density exceeding a pre-set therapeutic threshold;
(iii) the volumetric ultrasound beam is defocused in a region of a subject behind the heated target volume to avoid ultrasound hotspots;

control a HIFU therapy system to deliver ultrasound therapy to a patient; and heat the heating target volume with the HIFU system by controlling with the set of transducer switching commands to induce a therapeutic effect in the surface area to be treated and avoid in advertent ultrasound hotspots behind the heating target volume.

14. The medical apparatus as claimed in claim 2, wherein the ultrasound transducer element model predicts a path which ultrasound generated by a particular transducer element travels.

15. The medical apparatus of claim 2, wherein the transducer switching commands are determined such that the volumetric ultrasound beam matches the shape of the surface area to be treated.

16. A medical apparatus configured to apply palliative ultrasound treatment to a surface area of a bone of a patient affected with bone cancer, the apparatus comprising:

a high-intensity focused ultrasound (HIFU) therapy system, provided with an ultrasound transducer array configured to emit a volumetric ultrasound beam to heat a target volume within a subject, the ultrasound transducer array includes a plurality of ultrasound transducer elements arranged in a geometrical pattern, the individual ultrasound transducer elements being activated to emit the volumetric ultrasound beam wherein the geometrical pattern with a location and orientation of the transducer array defines a geometric focus;

a memory configured for storing machine executable instructions;

a processor configured to execute the machine executable instructions to:
receive surface data, wherein the surface data is indicative of a location and shape of the surface area to be treated of the bone affected with bone cancer;
calculate a set of transducer switching commands using an ultrasound transducer element model wherein the set of transducer switching commands comprises an intensity level for each of the ultrasound transducer elements either above or below a predetermined intensity for controlling a cross sectional shape of the volumetric ultrasound beam to encompass the surface area to be treated;
control the ultrasound transducer array to orient a principal axis of the volumetric ultrasound beam along an ultrasound propagation direction intersecting the surface area to be treated;
control the ultrasound transducer array to focus the volumetric ultrasound beam such that:
(i) the volumetric ultrasound beam has the cross section in a volumetric ultrasound beam's near field at the location of the surface area to be treated transverse to the principal axis corresponding to the surface area to be treated;
(ii) in the cross section corresponding to the surface area to be treated, the volumetric ultrasound beam has an energy density exceeding a pre-set therapeutic threshold at which the threshold nerve cells of the surface area are heated and deactivated to reduce pain suffered by the patient with the bone cancer;
(iii) the volumetric ultrasound beam is defocused in a region behind the surface area to be treated to move the geometric focus outside of the subject or to enlarge the geometric focus region such that only partial or no constructive interference occurs in the geometric focus region to eliminate small high energy areas to avoid ultrasound hotspots; and wherein the HIFU therapy system is controlled by the processor to deliver ultrasound therapy to the subject.

17. The medical apparatus of claim 2, wherein the ultrasound transducer element model is determined by projecting the surface area onto the ultrasound transducer array.

18. The medical apparatus of claim 1, wherein the ultrasound transducer array is operated in an unfocused mode to reduce a chance of destructive interference in the volumetric ultrasound beam.

* * * * *